Figure 1:
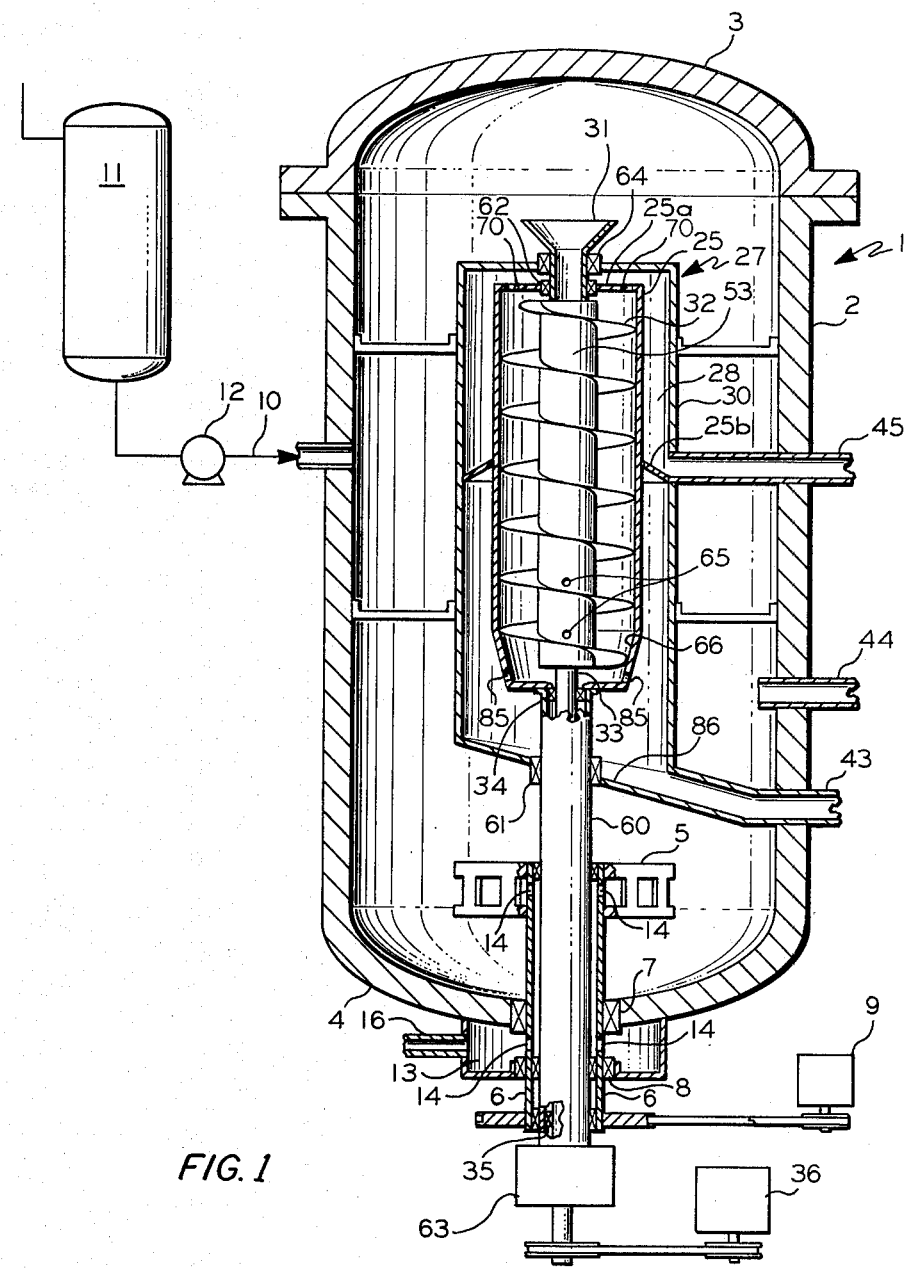

United States Patent [19]

Hitzman et al.

[11] 4,342,835

[45] Aug. 3, 1982

[54] FERMENTATION PROCESS AND APPARATUS

[75] Inventors: Donald O. Hitzman; Thomas R. Hopkins, both of Bartlesville, Okla.

[73] Assignee: Provesta Corporation, Bartlesville, Okla.

[21] Appl. No.: 193,873

[22] Filed: Oct. 3, 1980

[51] Int. Cl.³ .............................................. C12N 1/16
[52] U.S. Cl. ..................................... 435/255; 435/68; 435/243; 435/253; 435/313; 435/315; 435/316; 435/803; 435/804
[58] Field of Search ............... 435/312, 313, 314, 315, 435/316, 801, 803, 804, 812, 813, 819, 243, 261, 68, 253, 255

[56] References Cited

U.S. PATENT DOCUMENTS

| | | | |
|---|---|---|---|
| 2,244,902 | 6/1941 | Stich | 435/316 X |
| 2,952,588 | 9/1960 | Rinderer | 435/316 X |
| 3,114,677 | 12/1963 | Stich | 435/316 X |
| 3,528,889 | 9/1970 | Portno | 195/135 |
| 3,642,578 | 2/1972 | Hitzman et al. | 435/106 X |
| 3,693,325 | 9/1972 | Muller | 195/135 X |
| 3,957,585 | 5/1976 | Malick | 195/109 |
| 3,982,998 | 9/1976 | Hitzman et al. | 435/247 X |
| 4,029,724 | 6/1977 | Muller et al. | 195/142 X |
| 4,097,339 | 6/1978 | Marwil | 435/812 X |
| 4,169,010 | 9/1979 | Marwil | 435/812 X |

OTHER PUBLICATIONS

Kirk-Othmer Ency. of Chem. Tech., 2nd Ed., vol. 4, pp. 730-745, 1964.
Sharples Centrifuges Advertisement.
Sharples Brochure Bulletin, (1287-B).

Primary Examiner—Robert J. Warden

[57] ABSTRACT

Foam in a fermentation process is subjected to a centrifugal action causing a three layer separation. The three layers (gas, cell depleted liquid and cell rich liquid) are in contact with each other inside of the fermentation vessel.

17 Claims, 1 Drawing Figure

FERMENTATION PROCESS AND APPARATUS

This invention relates to an improved process and apparatus for separating multiphase mixtures internally in a fermenter. More specifically the invention relates to a process and apparatus wherein three phase systems from a biological conversion process are subjected inside of the fermenter to a centrifuge action resulting in three distinct streams.

BACKGROUND OF THE INVENTION

Biological processes have been used for centuries, for instance, in the production of beer and wine. Recently, single cell protein processes have become a field of significant research among the biological processes. Whereas broadly speaking biological processes include all operations involving reactions between living materials and non living materials, in the present specification and claims a more limited definition of a biological process is used. Here a biological process is intended to refer to processes involving microorganism fermentation in a fluid environment. Such microorganisms may be, e.g. bacteria or yeasts, and such fluid environments include foam environments.

One well known biological process to which this invention is applicable is a fermentation process for the production of single cell protein. A presently preferred example for such a process is described in U.S. Pat. Nos. 3,642,578 and 3,982,998. Generally, in a single cell protein fermentation process an aerobic fermentation involving a microorganism and a nutrient fluid is carried out in the presence of free oxygen supplied for instance by the injection of air. In a fermenter generally the nutrient fluid together with the microorganism are subjected to gas injection. A foam is formed in the upper portion of the fermenter whereas the lower portion of the fermenter generally contains a liquid. The foam formed is broken in a foam breaker and from this foam breaker gas is removed whereas the fluid remains in the fermenter.

From the bottom of the fermenter a microorganism containing fluid is usually withdrawn, subjected to a solid/liquid separation step, e.g., in a wash centrifuge and the recovered washed microorganism mass is thereafter dried to obtain the final product. The fluid removed during such a solid/liquid separation step contains still valuable ingredients and is therefore generally sterilized and thereafter returned to the fermenter. In the prior art procedures, the sterilization of this recycle liquid is necessary to avoid any contamination of the recycled stream. The fluid introduced into the fermenter has to be absolutely free of contaminating materials, such as contaminating organisms, in most biological process, since the smallest contamination with living organisms in the fermenter can destroy the entire reaction and result in undesired products, and a plant shut down and thus increased costs. Therefore, it has been proposed in the art to sterilize all recycled streams. This practice is today followed throughout the industry.

THE INVENTION

It is one object of this invention to provide a new fermentation process and apparatus for allowing simpler and more efficient recovery of the material to produce from the fermentation zone as compared to known processes.

Another object of this invention is to provide a fermentation process and apparatus with which cells from a fermentation process can be recovered in a concentrated stream.

A yet further object of this invention is to provide a fermentation process and apparatus in which a liquid stream essentially free of cell material can be recovered directly from the fermenter.

These and other objects, advantages, details, features and embodiments of this invention will become apparent to those skilled in the art from the following description, the appended claims and the drawing in which FIG. 1 shows schematically and in cross section an apparatus for carrying out the process of this invention.

In accordance with this invention a fermentation process is provided which comprises passing a multiphase mixture to be defined into a centrifuge cylinder and subjecting it to a rapid spinning movement inside of such a centrifuge cylinder to generate two fluids, namely a first fluid being rich in cells and second fluid being depleted of cells and comprising liquid and gas. The separation into an outermost cell rich area and inner cell depleted fluid area occurs inside of the centrifugal cylinder and inside of the fermenter. The efficiency of the separation depends upon the specific operating conditions and materials involved.

Preferably, the process of this invention uses a continuous scraping operation in which the first area of material which is in contact with the centrifuge cylinder and which is radically outermost layer is scraped from the wall and moved in axial direction mechanically toward a discharge means. This enables the use of a stronger centrifugal action and thereby a higher enrichment of cellular material in the outermost layer of cell rich fluid which without such scraping action would build up on the centrifuge walls.

The multiphase mixture referred to frequently is a foam. The multiphase mixture always comprises a gas phase, a liquid and a cell phase. In single cell protein (SCP) fermentation procedures the product to be withdrawn from the fermentation operation is the phase that is depleted of liquid and rich in cells. In other biological process the product may be the liquid product and thus may be the liquid phase depleted in cells. An example for the latter would be an alcohol producing fermentation.

The process of this invention is applicable to aerobic systems, i.e., systems in which $O_2$ is added to the fermenter, as well as to anaerobic systems, in which, e.g., $N_2$ or no gas at all is added; in the latter environment the cells during fermentation produce gas, such as $CO_2$ in an alcohol fermentation for the production of ethanol.

In a preferred embodiment of this invention, either the cell rich fluid or the cell depleted liquid is recycled to the fermentation. Neither fluid has to be sterilized because the recycling is done within a sterile environment. For instance, in a fermentation operation to produce alcohol or gum, the cell rich fluid is recycled and these recycled organisms are reused to produce more of the desired product. Therefore it is possible to operate in a very efficient manner despite the fact that, e.g., the alcohol concentration in the withdrawn cell depleted fluid is kept low at say 6–8 vol. % for highest cell activity. The same reasoning is true in case liquid products other than ethanol are produced that are inhibitory to organism growth, such as butanol, acetone, isopropanol, etc.

A further variation of the process is the removal of the liquid products in the stream of all depleted fluid under vacuum. This operation enhances the bursting of gas bubbles in the foam; furthermore, some solvents and/or product fluids may be partially or completely evaporated under the low pressure to facilitate their recovery or separation from the cells entrained in the cell depleted fluid.

More specifically, the process of this invention comprises subjecting a mixture of a growth medium and a microorganism to a fermentation in a fermenter. In this fermenter, a three phase mixture of gas, liquid and cells is generated. This three phase mixture is separated inside of the fermenter into a fluid comprising a gas phase and a liquid phase depleted of cells and into a cell rich phase depleted of liquid. This separation is done in a centrifuge cylinder arranged within the fermenter. In the process of this invention, the liquid depleted cell phase is in contact with the internal cylindrical surface of the centrifuge cylinder. At least a portion of the fluid phase and/or the cell rich phase is withdrawn from the fermenter.

In accordance with a second embodiment of this invention, an apparatus for carrying out a fermentation process as described is provided. This apparatus comprises a housing with inlet and outlet conduits. A centrifuge is arranged within the housing and this centrifuge comprises a centrifuge cylinder having an inner surface arranged and designed for receiving fluid material in a substantially tangential movement on this inner cylindrical surface. A conduit for receiving and conveying fluid comprising a liquid product depleted of fermentation cells, and a cell product conduit for receiving and conveying cell rich fluid product depleted of liquid from the centrifuge cylinder described are associated with the centrifuge. The apparatus is provided with means for subjecting a multiphase material comprising gas phase, a liquid phase, and a cell phase to a rapid movement having a substantial tangential component with respect to the inner cylindrical surface of the centrifuge. This rapid movement inside of the centrifuge cylinder causes the generation of the two fluids and their separation.

To allow the use of the apparatus with a higher centrifuge efficiency, there is preferably provided a scraper arranged within the centrifuge which is designed and arranged in the centrifuge cylinder for coaxial rotation with respect to this inner cylindrical surface and for advancing cell rich material along the inner cylindrical surface toward the cell product conduit. This scraper may have essentially helical structure. The rotation of such a scraper causes the material in contact with the scraper to be advanced in axial direction. Basically, the centrifuge and scraper may be a known device such as a Sharples centrifuge; the arrangement of the centrifuge inside of the fermenter in accordance with this invention may, however, require certain modifications.

Process and apparatus of this invention can be used in connection with fermentation processes of various kinds. The gas phase frequently is an oxygen supplying phase but can also be a phase free of any free oxygen. An example for a process wherein the gas phase is an oxygen supplying phase would be an aerobic single cell protein fermentation process. Such a process is the presently preferred application of the invention. Another example for the application of the process and apparatus of this invention is a process wherein the cells themselves produce $CO_2$ which causes foaming. Other operations may be anaerobic systems in which nitrogen or no gas at all are injected. As mentioned above, the actual product of the process may be the cells but may also be the liquid phase. Alcohol and water soluble gums would be examples of products recovered from the liquid phase of a fermentation process.

The invention will be still further understood from the following description of the drawing:

FIG. 1 is a cross sectional view of a fermentation apparatus 1 in accordance with this invention. The fermentation apparatus 1 comprises a housing 2 of essentially cylindrical shape which at the top portion is covered with a lid section 3. At the lower end of the cylindrical section 2 the housing is closed with a bottom section 4.

Into the housing 2 feed material can be introduced via conduit 10 from a supply 11 by means of a pump 12. Inside of the housing 2 a turbine 5 is arranged connected to a hollow shaft 6. This hollow shaft 6 is supported in bearings 7 and 8 and arranged for high speed rotation. A motor drive unit 9 for rotating the hollow shaft 6 and the turbine 5 is operatively connected thereto.

For the introduction of air into the turbine a chamber 13 is attached to the bottom section 4 of the housing. Passages 14 are provided in the hollow shaft 6. Air introduced into the chamber 13 via line 16 therefor can pass through the hollow shaft 6 into the turbine 5 and leave the turbine 5 in the interior of the housing generating small bubbles and creating the aeration of the fermentation mass inside of the housing 2.

Inside of the housing 2 a concentrating centrifuge 27 is arranged. This centrifuge comprises a cylindrical housing 30 coaxially arranged inside of said housing 2 providing an annular space 28 between the centrifuge housing 30 and centrifuge tube 25. In this annular space 28 fluid flows from holes 70 in the top 25a of the tube 25 toward the weir 25b and out of housing 2 through outlet 45. Inside of the centrifuge tube 25 a helically shaped rotor element 32 on a coaxial hollow rotor 53 is provided. This hollow rotor 53 is attached to a shaft 33 which is supported for rotation by means of bearings 34 and 35 (at the lower end). A motor drive unit 36 is operatively connected with the shaft 33 attached to the rotor 53 for rapid rotation of helical element 32 within the centrifuge tube 25.

Centrifuge tube 25 is also rotatable within the housing 30 by means of hollow shaft 60 which is concentric with shaft 33 of the rotor 53. Hollow shaft 60 is mounted for rotation on bearings 61 and 62. Hollow shaft 60 and shaft 33 are both connected for rotation in the same direction but at different speeds of rotation through gear box 63 and motor drive unit 36. Hollow rotor 53 extends through the top 25a of centrifuge tube 25 and housing 30 to frustoconical member 31 which is rotatable with hollow rotor 53 through bearings 62 and 64. Foam and/or liquid entering frustoconical member 31 progresses downward through hollow rotor 53 and out through holes 65 for separation or concentration during the rotation of the hollow rotor and centrifuge tube 25. For example, with this hollow rotor 53 and the helical rotor element 32 operating at 4000 rpm and centrifuge tube 25 operating at 5000 rpm the fluid or foam from holes 65 containing organisms would be separated as the liquid and gas phases move upward and discharge out of centrifuge tube 25 through holes 70 into annular space 28. The helical rotor element 32 acts as a scraper during its coaxial rotation with respect to the inner cylindrical surface of the centrifuge cylinder 25. The liquid is collected on the weir 25b and passes out of the housing 2 through outlet 45. The weir 25b is attached to the inside wall of housing 30 on one edge and spaced from the outside of centrifuge tube 25 a sufficient distance to allow rotation. The cell rich fluid phase or paste would then move downward along the beach 66 of centrifuge tube 25 and out through holes 85 collecting on the sloping bottom 86 of the housing 30. This cell rich fluid may leave the fermenter through outlet 43. Tubing 44 through the housing tube can be utilized for recycling the liquid phase from outlet 45 or the cell rich phase from outlet 43 as desired; the valves or control mechanisms used in such a recycle have been omitted from the drawing. It is a particular advantage of this invention that a recycle of either cell rich paste or of cell depleted liquid is possible while these products are still in the sterile environment.

To illustrate the invention more specifically, the following is a possible operation and exemplification of the invention not intended to limit the scope thereof unduly.

A yeast which produces a product, i.e., extra celluar metabolite, is cultured in medium with nutrients adequate to support the population desired. The product, which can either be inhibitory at higher concentration, for example alcohol or solvents, or reutilized (i.e., amino acids such as lysine) should be withdrawn continually from the fermenter. Taking a case of alcohol production, the yeast, S. cervesiae, is grown on molasses with adequate minerals, phosphate, magnesium, etc. Once the cell density is reached that is desired, the centrifuge is turned on. The foam caused by $CO_2$ production which contains a higher concentration of cells is passed continually through the centrifuge. The cells are returned to the fermenter in the form of the cell rich paste while the effluent contains alcohol to a concentration of 5-8%. The alcohol can be stripped from the liquid cell depleted effluent stream and the liquid phase can be recycled or otherwise disposed of. In most cases, it would be refortified with more molasses for another pass. This keeps the alcohol concentration down to a level where the yeast is most active; the yeast slows down as alcohol level builds up and fermentation stops at about 10-12% alcohol concentration. The return of the cells to the fermenter builds up a higher cell density so the fermenter rate of alcohol production increases.

Should the process be designed to produce single cell protein, the process involves growing the cells to high densities, then removing the cells while recirculating the supernatant. For example, *Pichia pastoris* can be grown to levels of 120 grams per liter, on methanol being fed at a concentration of 40%, but the alcohol concentration in the fermenter is maintained at 0-0.05%. The temperature would be 30° C. and the pH at 3.5 with $NH_3$ being supplied for pH adjustment and nitrogen content. The recycled medium is refortified with phosphate, magnesium and trace minerals as needed. The retention time in the fermenter can be about 8-10 hrs. In this case, the supernatant could contain an extracellular product such as lysine, methionine, and tryptophan which could be removed by any extractive technique and recovered as a marketable product prior to the return of the supernatant to fermenter.

Reasonable variation and modification which will become apparent to those skilled in the art can be made in this invention without departing from the spirit and scope thereof.

We claim:
1. A fermentation process comprising
   (a) subjecting a mixture of a growth medium and a microorganism to a fermentation in a fermenter,
   (b) generating a three phase mixture of gas, liquid and cells in said fermenter,
   (c) carrying out a separation inside of said fermenter by passing the three phase mixture into a centrifuge cylinder,
   (d) subjecting said three phase mixture in said centrifuge cylinder to a rapid spinning movement in contact with said centrifuge cylinder and thereby generating in at least a significant portion of the axial length of the centrifuge cylinder a first zone of material in contact with the centrifuge cylinder which material is rich in cells and depleted in liquid, a second zone being depleted of cellular material and rich in liquid,
   (e) withdrawing a first fluid comprising said gas phase and a liquid depleted of cells as well as a separate second fluid being enriched in said cells and depleted of said liquid as two separate streams from said centrifuge cylinder, and
   (f) recovering at least a portion of said first and/or second fluid from the fermenter as the product of the process.

2. Process in accordance with claim 1 comprising scraping along the inner cylindrical surface of the centrifuge cylinder and advancing said second fluid depleted of the liquid toward a location of withdrawal from where said cells are withdrawn from said centrifuge.

3. Process in accordance with claim 1 comprising withdrawing a portion of said second fluid from the fermenter and releasing a portion of said second fluid from the centrifuge into the fermenter and back into contact with the three phase fermentation mixture.

4. Process in accordance with claim 1 comprising
   (a) recovering said second fluid and separating a dried cell product from said second fluid, and
   (b) reintroducing at least a portion of the liquid of said first fluid while maintaining it under conditions free from outside contamination into said fermenter and into contact with said three phase mixture.

5. An apparatus for carrying out a fermentation process comprising
   (a) a closed fermenter housing,
   (b) a centrifuge arranged within said closed fermenter housing and comprising
      (aa) a centrifuge cylinder having an inner cylindrical surface arranged and designed for receiving a three phase mixture in a substantially tangential movement on said inner cylindrical surface,
      (bb) a first fluid product conduit for receiving and conveying liquid product depleted of fermentation cells and gas from the centrifuge cylinder
      (cc) a cell product conduit for receiving and conveying a second fluid rich in cell material from the centrifuge cylinder,
      (dd) at least one of said product conduits providing a connection from said centrifuge through the confining wall of said closed fermenter housing to the outside thereof
   (c) a feed inlet conduit operatively connected with said closed fermenter housing adapted for introduction of feed fluid into said closed fermenter housing and into the space within said closed fermenter housing surrounding said centrifuge, (d) centrifuge inlet means to inject a three phase mixture from inside of said closed fermenter housing into said centrifuge cylinder and with a substantial speed component tangentially with respect to said inner cylindrical surface.

6. An apparatus in accordance with claim 5 further comprising a scraper arranged and designed for coaxial rotation with respect to the inner cylindrical surface of the centrifuge cylinder and for advancing said second fluid along the inner cylindrical surface toward said cell product conduit.

7. An apparatus in accordance with claim 6 wherein said scraper is of an essentially helical structure contacting said inner cylindrical surface.

8. An apparatus in accordance with claim 6 wherein said scraper is connected to a motordrive for subjecting said scraper to rapid rotation so that said scraper provides for both advancing of the cell material along the centrifuge wall and at least some acceleration of the multiphase material to said rapid movement.

9. An apparatus in accordance with claim 5 wherein said centrifuge comprises a stationary centrifuge housing, within said centrifuge housing said centrifuge cylinder and coaxially within said centrifuge cylinder, a rotor cylinder, the interior of which communicates with the space between said cylindrical centrifuge housing and said fermenter housing, which rotor cylinder is provided with at least one opening for essentially tangential discharge of fluid within said rotor cylinder, and wherein drive means are operatively connected to said rotor cylinder permitting it to be put into rapid rotation.

10. Apparatus in accordance with claim 9 wherein a helical scraper is attached to the outside of said rotor, the external edge of said scraper being in close vicinity of said inner cylindrical surface of said centrifuge cylinder.

11. An apparatus in accordance with claim 9 or 10 wherein said fermenter housing and said centrifuge housing are cylindrical and coaxially arranged.

12. An apparatus in accordance with claim 9 wherein said centrifuge housing is arranged essentially vertically and is closed with an inclined bottom section communicating with said cell product conduit.

13. An apparatus in accordance with one of the claims 9, 10 or 12 wherein said centrifuge housing is essentially cylindrical and said centrifuge cylinder is arranged coaxially within said centrifuge housing.

14. An apparatus in accordance with claim 10 wherein in said centrifuge cylinder or in the end closures thereof there is provided at least one first opening at or near the first end of said centrifuge cylinder for a light fluid and at least one second opening at or near the second end of said centrifuge cylinder for a heavy fluid, said openings permitting both fluids to flow from said centrifuge cylinder into the space between said centrifuge cylinder into the space between said centrifuge cylinder and said stationary centrifuge housing, both said first fluid product conduit and said cell product conduit being connected to withdraw the respective products from said centrifuge housing.

15. An apparatus in accordance with one of the claims 5 to 10, 12 or 14 comprising gas injection means connected with said fermenter housing for injecting gas into said fermenter housing.

16. An apparatus in accordance with claim 15 wherein said gas injection means comprise a turbine-type element operatively connected to both a gas inlet line and drive means allowing the discharge of gas inside of said fermenter from said turbine-type element put into rapid rotation by said drive means.

17. An apparatus in accordance with one of the claims 5 to 10, 12 or 14 wherein said centrifugal inlet means comprises a conduit connecting the space in the upper portion of said closed fermenter housing with the inside of said centrifuge cylinder.

* * * * *